United States Patent
Dürr et al.

[11] Patent Number: 5,122,059
[45] Date of Patent: Jun. 16, 1992

[54] ENOSSAL IMPLANT FOR A FIRMLY SEATED TOOTH REPLACEMENT

[75] Inventors: Walter Dürr, Remchingen; Axel Kirsch, Filderstadt, both of Fed. Rep. of Germany

[73] Assignees: Eberle Medizintechnische Element GmbH; IMZ-Fertigungs-und Vertriebs-Gesellschaft fuer dentale Technologie mbH, both of Fed. Rep. of Germany

[21] Appl. No.: 756,284

[22] Filed: Sep. 6, 1991

[30] Foreign Application Priority Data

Sep. 8, 1990 [DE] Fed. Rep. of Germany ....... 4028857

[51] Int. Cl.⁵ .............................................. A61C 8/00
[52] U.S. Cl. .................................... 433/173; 433/169
[58] Field of Search ................ 433/169, 173, 174, 175

[56] References Cited

U.S. PATENT DOCUMENTS

| | | | |
|---|---|---|---|
| 4,552,532 | 11/1985 | Mozsary | 433/173 |
| 4,746,293 | 5/1988 | Lundgren et al. | 433/173 |
| 4,756,689 | 7/1988 | Lundgren et al. | 433/173 |
| 4,793,808 | 12/1988 | Kirsch | 433/173 |
| 4,872,839 | 10/1989 | Brajnovic | 433/173 |
| 4,927,363 | 5/1990 | Schneider | 433/173 |
| 4,955,811 | 9/1990 | Lazzara et al. | 433/173 |
| 4,993,950 | 2/1991 | Mensor, Jr. | 433/173 |
| 5,026,280 | 6/1991 | Dürr et al. | 433/175 |
| 5,026,285 | 6/1991 | Dürr et al. | 433/173 |
| 5,040,982 | 8/1991 | Stefan-Dogar | 433/173 |
| 5,049,072 | 9/1991 | Lueschen | 433/173 |
| 5,052,931 | 10/1991 | Kirsch | 433/173 |
| 5,071,351 | 12/1991 | Green, Jr. et al. | 433/173 |

Primary Examiner—John J. Wilson
Attorney, Agent, or Firm—Hill, Van Santen, Steadman & Simpson

[57] ABSTRACT

An enossal implant for firmly seating a tooth replacement includes a fastening head on a metal implant post which is threadably secured into a base element, which is either a base body or a metal spacer threaded into the base body. To prevent twisting between the post and the base element, the base element has a recess for receiving an intermediate retaining ring formed of a plastic material which has smooth faces, and the ring is entrapped between a shoulder in the base element and a shoulder on the implant post and interlocking depressions are formed in either the recess and/or the shoulder of the post so that during threading-in of the post, the retaining ring is deformed to fill the recesses to restrain twisting therebetween.

11 Claims, 2 Drawing Sheets

ENOSSAL IMPLANT FOR A FIRMLY SEATED TOOTH REPLACEMENT

BACKGROUND OF THE INVENTION

The present invention is directed to an enossal implant for a firmly seated tooth replacement, which implant includes a fastening device having a fastening head in an implant post connectible to a base element via a thread connection, said base element being selected from a base body and a metal spacer part threadably recieved in the base body and the distal end of the base element being separated from a portion of the implant post by a concentrically surrounding intermediate element made of an elastic plastic material, such as polyoxymethylene.

U.S. Pat. No. 5,026,280, whose disclosure is incorporated herein by reference thereto and which claims priority from German Application 38 39 274, discloses an enossal implant in which a metallic spacer part is threaded into one end of a threaded bore of a base body until it engages an upper shoulder along the upper edge of the body. A plastic intermediate element concentrically surrounds an implant post which is threadably engaged in the spacer art so that the intermediate element is entrapped between the spacer part and the tooth replacement. The implant post can be threaded into the spacer part while pressing a bearing surface of the tooth replacement facing the intermediate element onto a stop shoulder of the intermediate element remote from the spacer part. The enossal implant has excellent cushioning characteristics, but does not insure a satisfactory restraint to twisting of the tooth replacement with respect to the base body and, therefore, the jaw bone, unless special measures, such as bending and the like, are adopted. The known implant is, therefore, only suitable to a limited extent for use as a single tooth implant. This unsatisfactory solution for providing a restraint to twisting can also be at a disadvantage in other cases.

U.S. Pat. No. 5,026,285, whose disclosure is incorporated herein by reference thereto and which claims priority from German Application 39 17 690, is directed to an enossal single tooth implant for a firmly seated tooth replacement in which the spacer part comprises a two-part metallic spacer bushing which can be threaded into the base body and whose two parts are locked to one another and to the base body. Such locking together will lead to a twist-restrained connection between the base body and the spacer bushing's top and bottom parts. If a corresponding twist-restrained fixing is insured, this enables the tooth replacement to be connected in a twist-restrained manner to one of the last-mentioned parts of the spacer bushing. The known enossal single tooth implant has proven satisfactory, but makes it necessary to use special locking tools which can be difficult to use in certain cases.

SUMMARY OF THE INVENTION

The object of the present invention is to provide an enossal implant with which as simple means as possible brings about at least a substantial restraint to twisting of the implant post and, therefore, the fastening head of the post with respect to a base body or element and, therefore, the jaw bone or body tissue.

To accomplish these goals, the present invention is directed to an improvement of an enossal implant for firmly seated tooth replacement having a fastening device including a fastening head and a metal implant post connectible to a base element which is selected from a base body having a threaded bore or a metallic spacer which is threadably received in the bore of the base body and projects therefrom. The implant post is concentrically surrounded close to the upper edge of the base element by an intermediate element made from an elastic material, for example, in particular, a polyoxymethylene material. The improvements are means for resisting twisting, which includes the intermediate element being a retaining ring with substantially planar, smooth end faces, said base element, close to an upper circumferential edge, having an annular recess for receiving the retaining ring and being provided with a stop shoulder for the closest end face of the retaining ring which is received with a flush reception in the recess with at least part of the surface of the base element and the implant post coming into pressing engagement with the retaining ring on a threading of the implant post into the base element, said base element and/or the implant post being provided with interlocking depressions, into which the material of the retaining ring will be deformed under the threading in pressure to form a positive twist restraint between the implant element adjacent the base element to form the means for resisting twisting.

At least part of the interlocking depression is located on a circumferential surface of the annular recess and/or an area of the implant post and/or spacer part adjacent to a ring shoulder of the post.

The invention also proposes at least part of the interlocking depression be provided on the stop shoulder of the annular recess and/or the ring shoulder.

According to the invention, the stop shoulder and/or ring shoulder can have several pocket-like end depressions.

According to a further development of the invention, four pocket-like end depressions are uniformly distributed in a circumferential direction on the stop shoulder and/or ring shoulder.

The invention also proposes that the stop shoulder and ring shoulders have radial serrations. The radial serrations may be constructed in a sawtooth manner in such a way that during the threading in process, there is a ratchet action aiding the threading-in, but hindering unthreading or unscrewing with respect to the engaged face of the retaining ring.

The invention also utilizes radial serrations, which are constructed in a crown-like manner.

According to another embodiment of the invention, the implant post can be threaded directly into the base body or can be threaded into a metallic spacer which, in turn, is threaded into a base body.

According to the invention, the implant post may have a polygonal fastening head for the tooth replacement.

The invention is based on the surprising findings that it is possible to obtain a substantially twist-resistant implant in that a plastic retaining ring is deformed in such a way on threading the implant post into either the base body or a metal spacer, which is threaded into the base body, that a positive twisting restraining in conjunction with the interlocking depressions of the base element and with those of the implant post. For example, this can be brought about by radial serrations of the proximal ring shoulder of the implant post, which initially slide over the retaining ring during the introduction of the implant post and subsequently the retaining ring material engages, accompanied by deformation, into the radial serrations. The same is achieved by interlocking depressions on a stop shoulder of the annular recess of the implant post or spacer part and, preferably, be interlocking depressions which are formed by individual pockets which can be used for certain applications for attachment of a tool or for producing a plug connection with further build-up elements.

The inventive retaining ring can be used not only for obtaining a twisting restraint between the base element and implant post threaded directly into the same and can also be used, in the case of implants as described in the above-mentioned U.S. Pat. No. 5,026,280, for example those in which, first, a spacer part is threaded into the base body and then the implant post is threaded into the spacer part. Optionally, the inventive twist restraint can be in multi-step form, for example between the base body and spacer part or a bushing, on the other hand, and between the spacer part or bushing and the implant post on the other.

This invention is particularly suitable in conjunction with providing means for twist-restraining construction for a single tooth implant or the like.

Other advantages andd features of the invention will be readily apparent from the following description of the preferred embodiments, the drawings and claims.

DESCRIPTION OF THE PREFERRED EMBODIMENTS

Figure 1:
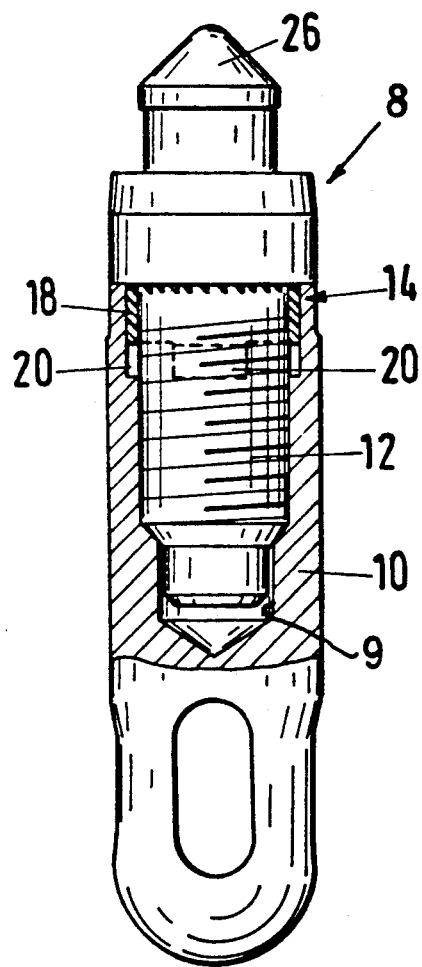
FIG. 1 is an elevational view with portions in cross section for purposes of illustration of an enossal implant including a base body, an intermediate ring and an implant post.

The principles of the present invention are particularly useful in the enossal implant, generally indicated at 8 in FIG. 1, which is composed of a base body 10, an implant post 12, and an intemediate plastic retaining ring 18.

Figure 2:
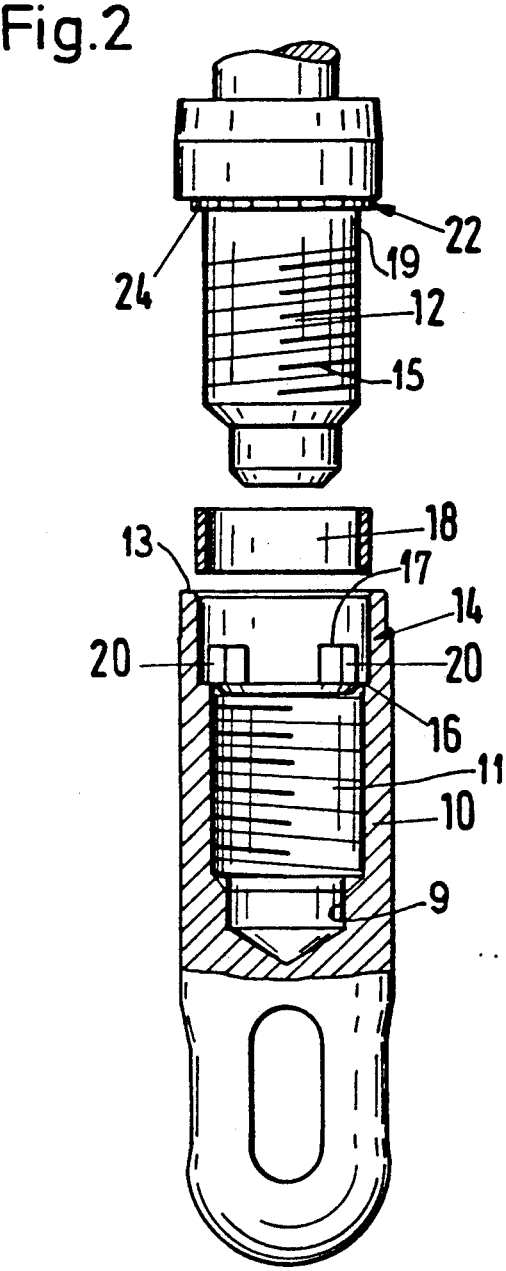
FIG. 2 is an exploded view of the implant post, intermediate ring and base body with portions in cross section.
Figure 3:
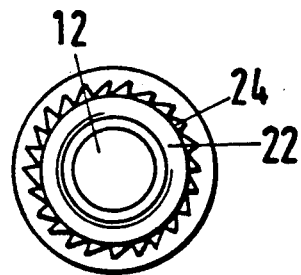
FIG. 3 is a bottom end view of the implant post of FIGS. 1 and 2.
Figure 4:
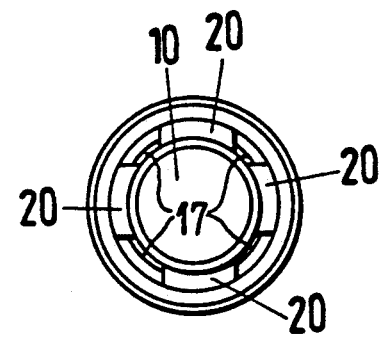
FIG. 4 is a top plan view of the base body of the implant post of FIGS. 1 and 2.

The base body 10 is preferably made of titanium metal has its outer surfaces coated with hydroxyapatite or TPS, which surfaces come into contact with the body tissue. The function of this body 10 corresponds to that of the implants disclosed in the above-mentioned U.S. Pat. No. 5,026,280. The base body 10 is provided with an axially extending bore 9, which has a portion with internal threads 11 and the bore 9 opens to one end of the member 10 to form a shoulder 13. Adjacent the shoulder 13, the base body 10 is provided with an annular recess 14, which is of a larger diameter than the portion having the internal threads 11. An internal stop shoulder 16 is formed between the enlarged diameter recess 14 and the portion of the bore 9 having the threads 11. As illustrated best in FIGS. 2 and 4, the recess has four annularly spaced depressions 20, which are formed by tongues 17 that extend upward from the shoulder 16. These tongues 17 terminate from the uppper shoulder 13 a distance slightly less than the axial extent of a retaining ring 18, which is dimensioned to be received in the recess 14.

The implant post 12 has a threaded portion 15 for threading into the threads 11 of the base body 10. Above the threaded portions is a smooth cylinddrical portion 19, which is adjacent a ring shoulder 22 that is provided with downwardly extending sawtooth-like, crown-like radial serrations 24. As illustrated in FIG. 1, when the implant post 12 is threaded into the base body 10, the ring 18 is entrapped between the inner surface of the recess 14 and the portion 19 of the post and has the end faces engaged with the sawtooth-like radial serrations 24 of the shoulder 22 and the tongues 17 in the recess 14.

The implant post 12, to enable tooth replacement to be secured thereon, has a fastening head 26, which can be constructed conically as in the illustrated embodiment. It is also contemplated that the fastening head will have a circumferentially polygonal shape and make it possible to engage in a twist-resistant manner a tooth replacement on the post 12.

In the illustrated embodiment of the invention, it is realized that on threading the implant post 12 into the base body 10, the plastic retaining ring 18 is subjected to increasing compression within the annular recess 14. The depressions 20 formed by the tongues extending upward from the shoulder 16 of the annular recess, on the one hand, and the radial serrations 24 on the ring shoulder 22 of the implant post coact to form interlocking depressions into which the plastic material of the retaining ring 18 will flow to an ever-increasing extent as a result of the viscoelastic properties which will occur during tightening of the implant post. Thus, when the implant post is threaded in so that the shoulder 22 contacts the upper edge or surface 13, a twist-restraining interlocking connection occurs between the base body 10 and the post 12 and, therefore, also the fastening head 26. This makes it possible to anchor the tooth replacement in a twist-restrained manner in the body tissue, particularly if the fastening head 26 is constructed as a polygonal, for example as a hexagonal post. In spite of the twisting restraint obtained in this way, if necessary, the implant post 12 can still be unthreaded from the base body 10, which might lead to partial destruction of the retaining ring. However, on again introducing the implant post using a new retaining ring, it once again is easily possible to obtain the twist-resistant connection between the parts.

Although various minor modifications may be suggested by those versed in the art, it should be understood that we wish to embody within the scope of the patent granted hereon all such modifications as reasonably and properly come within the scope of our contribution to the art.

We claim:

1. In an enossal implant for a firmly seated tooth replacement having a fastening device including a fastening head on a metal implant post which is threadably connected in a threaded bore of a base element, which is selected from a base body having a threaded bore and a metal spacer having a threaded bore and being threadably received in the threaded bore of the base body to extend from one end of the base body, the implant post being zonally concentrically surrounded close to the distal edge of the base element by an intermediate element made from an elastic plastic material, the improvements comprising means for resisting twisting between the implant post and the base element, said means including the intermediate element being a cylindrical retaining ring with substantially planar smooth end faces, said base element, adjacent an open end of the threaded bore, having an annular recess for receiving the retaining ring, said recess being provided with a stop shoulder for engaging one of the faces of the retaining ring as it is received in the recess, said recess having an axial extension less than the length of the retaining ring, said implant post having a ring shoulder engaging the other of the end faces of the ring, and interlocking depressions being provided in one of the recess and the ring shoulder so that as the implant post is threaded into the base element, the material of the retaining ring is deformed under the compression to cause formation of a positive twist resistance between the retaining ring, base element and implant post.

2. In an enossal implant according to claim 1, wherein the interlocking depressions are provided both in the annular recess and the ring shoulder.

3. In an enossal implant according to claim 1, wherein the interlocking depressions are provided on a stop shoulder of the annular recess and on the ring shoulder of the implant post.

4. In an enossal implant according to claim 3, wherein the stop shoulder has several pocket-like front depressions.

5. In an enossal implant according to claim 4, which includes four pocket-like front depressions being uniformly distributed in the circumferential direction of the stop shoulder.

6. In an enossal implant according to claim 3, wherein the interlocking depressions on at least one of the annular recess and ring shoulders are radial serrations.

7. In an enossal implant according to claim 6, wherein the radial serrations are constructed in a sawtooth manner so that during a threading-in process they form a ratchet action aiding threading-in and hindering unthreading and disengagement from the engaged face of the retaining ring.

8. In an enossal implant according to claim 6, wherein the radial serrations are constructed in a crown-like manner.

9. In an enossal implant according to claim 1, wherein the base element is the base body and the implant post is directly screwed therein.

10. In an enossal implant according to claim 1, wherein the implant post has a polygonal fastening head for the tooth replacement.

11. In an enossal implant according to claim 1, wherein the elastic plastic material of the retaining ring is a polyoxymethylene.

* * * * *